US008647271B2

(12) United States Patent
Müller et al.

(10) Patent No.: US 8,647,271 B2
(45) Date of Patent: Feb. 11, 2014

(54) HYDROGEL IMPLANT FOR SENSING METABOLITES IN BODY TISSUE

(75) Inventors: Achim Müller, Grossostheim (DE); Peter Herbrechtsmeier, Königstein (DE); Monika Knuth, Aschaffenburg (DE); Katharina Nikolaus, Aschaffenburg (DE)

(73) Assignee: Eyesense AG, Basel (CH)

( * ) Notice: Subject to any disclaimer, the term of this patent is extended or adjusted under 35 U.S.C. 154(b) by 751 days.

(21) Appl. No.: 12/601,524

(22) PCT Filed: May 23, 2008

(86) PCT No.: PCT/EP2008/056364
§ 371 (c)(1),
(2), (4) Date: Jun. 11, 2010

(87) PCT Pub. No.: WO2008/142158
PCT Pub. Date: Nov. 27, 2008

(65) Prior Publication Data
US 2010/0331634 A1    Dec. 30, 2010

Related U.S. Application Data

(60) Provisional application No. 60/924,669, filed on May 25, 2007.

(30) Foreign Application Priority Data

May 24, 2007    (DE) .................. 10 2007 024 642

(51) Int. Cl.
*A61B 5/00*    (2006.01)

(52) U.S. Cl.
USPC ........................................ 600/309

(58) Field of Classification Search
USPC ........................................ 600/309, 318, 325
See application file for complete search history.

(56) References Cited

U.S. PATENT DOCUMENTS

| | | | |
|---|---|---|---|
| 4,180,308 A * | 12/1979 | Mancini et al. | .......... 351/159.33 |
| 5,127,901 A | 7/1992 | Odrich | |
| 5,300,114 A | 4/1994 | Gwon et al. | |
| 5,404,951 A * | 4/1995 | Lai et al. | .......... 166/295 |
| 5,476,511 A | 12/1995 | Gwon et al. | |
| 5,508,317 A | 4/1996 | Muller | |

(Continued)

FOREIGN PATENT DOCUMENTS

| | | |
|---|---|---|
| EP | 0 637 490 A1 | 2/1995 |
| EP | 0 641 806 A2 | 3/1995 |

(Continued)

*Primary Examiner* — W B Perkey
*Assistant Examiner* — Linda B Smith
(74) *Attorney, Agent, or Firm* — Fanelli Haag & Kilger PLLC

(57) ABSTRACT

An implant (110) for detecting at least one analyte (126) in a body fluid, in particular an eye fluid, is proposed. The implant (110) is designed to be implanted in a tissue layer and/or a chamber of an eye of a patient, the implant (110) having a hydrogel matrix (110) with at least one hydrogel (114). The implant (110) also has sensor particles (116) dispersed in the hydrogel matrix (110), the sensor particles (116) having at least one sensor matrix (120) with a sensor matrix material (122) and at least one sensor material (124).

25 Claims, 3 Drawing Sheets

(56) References Cited

U.S. PATENT DOCUMENTS

| | | | |
|---|---|---|---|
| 5,545,423 A | 8/1996 | Soon-Shiong et al. | |
| 5,705,780 A * | 1/1998 | Bao | 204/157.15 |
| 6,329,485 B1 * | 12/2001 | Vanderbilt | 526/318.1 |
| 6,416,777 B1 | 7/2002 | Yaacobi | |
| 6,451,871 B1 | 9/2002 | Winterton et al. | |
| 6,485,703 B1 | 11/2002 | Cote' et al. | |
| 6,699,501 B1 | 3/2004 | Neu et al. | |
| 6,896,926 B2 | 5/2005 | Qiu et al. | |
| 6,926,965 B2 | 8/2005 | Qiu et al. | |
| 6,986,900 B2 | 1/2006 | Yaacobi | |
| 7,022,379 B2 | 4/2006 | Winterton et al. | |
| 7,228,159 B2 * | 6/2007 | Petersson et al. | 600/316 |
| 2001/0019406 A1 * | 9/2001 | Russell et al. | 356/124 |
| 2003/0149359 A1 * | 8/2003 | Smith | 600/437 |
| 2004/0062809 A1 * | 4/2004 | Honiger et al. | 424/486 |
| 2004/0157951 A1 | 8/2004 | Wolf | |
| 2005/0095174 A1 * | 5/2005 | Wolf | 422/82.08 |
| 2006/0105335 A1 | 5/2006 | Daehne et al. | |
| 2007/0035693 A1 * | 2/2007 | Back | 351/160 R |
| 2007/0105176 A1 | 5/2007 | Ibey et al. | |
| 2007/0122362 A1 * | 5/2007 | Giniger et al. | 424/53 |
| 2007/0122829 A1 * | 5/2007 | Ballerstadt et al. | 435/6 |
| 2007/0184222 A1 * | 8/2007 | Delouise et al. | 428/35.2 |
| 2007/0270675 A1 * | 11/2007 | Kane et al. | 600/315 |
| 2008/0020051 A1 | 1/2008 | Dahne et al. | |
| 2009/0264553 A1 * | 10/2009 | Chen et al. | 523/107 |

FOREIGN PATENT DOCUMENTS

| | | |
|---|---|---|
| EP | 0 790 258 A2 | 8/1997 |
| EP | 1 116 516 A1 | 7/2001 |
| WO | WO 96/24074 A1 | 8/1996 |
| WO | WO 97/19188 A1 | 5/1997 |
| WO | WO 99/47252 A2 | 9/1999 |
| WO | WO 99/47253 A1 | 9/1999 |
| WO | WO 00/03797 A1 | 1/2000 |
| WO | WO 00/77281 A1 | 12/2000 |
| WO | WO 01/13783 A1 | 3/2001 |
| WO | WO 02/17888 A2 | 3/2002 |
| WO | WO 02/087429 A1 | 11/2002 |
| WO | WO 2004/014540 A1 | 2/2004 |
| WO | WO 2004/064629 A1 | 8/2004 |
| WO | WO 2005/089727 A1 | 9/2005 |

\* cited by examiner

US 8,647,271 B2

HYDROGEL IMPLANT FOR SENSING METABOLITES IN BODY TISSUE

FIELD OF THE INVENTION

The invention relates to shaped hydrogel articles that are constructed in such a way that an analyte to be determined is able to diffuse freely in the aqueous phase of a hydrogel network, but the chemical or biochemical. sensor components are immobilized in the network. The external form and the mechanical properties of the shaped hydrogel article are optimized for implantation and for the implantation site. Shaped hydrogel articles of this kind can be used, for example, to detect analytes, in particular specific metabolites, in a body tissue, in particular a body fluid, In particular, the body tissue can be body tissue of an eye and the body fluid can be an eye fluid (e.g. aqueous humor, lacrimal fluid or interstitial fluid). The proposed shaped hydrogel article can, however, also be used in principle for other tissue types and/or types of body fluids.

The detection of the at least one analyte to be determined can range from a purely qualitative detection to a quantitative detection. Such detection methods can be used, for example, to determine a glucose concentration in the body tissue, for example in the eye fluid. Taking known correlations into account, it is then possible, from this analyte concentration or glucose concentration, to draw conclusions regarding, for example, a concentration of the analyte, in particular of the glucose, in other body fluids, for example in blood. In addition to glucose, the present invention can also be applied, alternatively or additionally, to other types of analytes.

PRIOR ART

Conventional systems for determining analyte or metabolite concentrations, in particular the blood glucose concentration, are generally based on the patient or a physician puncturing an area of skin, for example by means of a suitable lancet system, and in this way generating a blood sample. The analyte content of this sample is then analyzed using suitable measurement techniques, for example optical and/or electrochemical measurement techniques. In addition to detection in blood, detection can also be carried out in other body fluids, for example in urine.

In order to reduce the inconvenience that patients experience clue to the frequent generation of blood samples, various non-invasive or minimally invasive techniques have been developed for measuring analyte concentrations. Without limiting the scope of protection of the invention, the determination of blood glucose concentrations is discussed below, it being understood that other types of analytes or metabolites can of course also be detected.

One technique of measuring blood glucose concentrations is based on measuring glucose in body tissue and body fluids, in particular in eye fluids, for example lacrimal fluid, aqueous humor or interstitial fluid. Thus, for example, WO 01/13783 describes an ocular sensor for glucose, which is designed as an ophthalmic lens. The ocular sensor comprises a glucose receptor, which is marked with a first fluorescence label, and a glucose competitor, which is marked with a second fluorescence label ("donor"). The two fluorescence labels are chosen such that, when the competitor is hound to the receptor, the fluorescence of the second fluorescence label is quenched on account of a resonant fluorescence energy transfer. By monitoring the change in fluorescence intensity at a wavelength around the fluorescence maximum of the quenchable fluorescence label, it is possible to measure the proportion of the fluorescence-marked competitor that has been displaced by the glucose. In this way, the glucose concentration in the eye fluid can be determined. This measurement can in turn be used to draw conclusions regarding the blood glucose concentration. Other types of detection are also conceivable and are familiar to persons skilled in the art, for example a fluorescence detection of the first fluorescence label.

WO 02/087429 also describes a fluorescence photometer by means of which blood glucose concentrations can be determined by measuring the glucose concentration in an eye fluid. The device disclosed is able to measure two fluorescence intensities simultaneously at two different wavelengths.

The cited documents from the prior art represent only a small number of examples of how analytes can be detected by suitable sensors in an implant, for example an eye implant, and how their concentration can be determined. In most cases, however, a central aspect is the design of the implant, in particular of the eye implant itself, which has to satisfy numerous requirements and conditions for analysis. Hydrogels in particular have proven to be a suitable matrix material for such implants. Hydrogels are water-containing, but at least substantially water-insoluble polymers whose molecules are linked chemically, e.g. by covalent or ionic bonds, or physically, e.g. by entanglement of the polymer chains, to form a three-dimensional network. Hydrogels generally have hydrophilic polymer components, which have the effect that the hydrogels swell up in water to a considerably increased volume, while their material cohesion is at least substantially retained. Hydrogels have a high degree of biocompatibility and in most cases have tissue-like mechanical properties.

Shaped hydrogel articles with specific additives embedded in the hydrogel network are known from the prior art, hydrogel network being understood as a water-containing network constructed from a polymer which is either water-insoluble per se or has been made water-insoluble by suitable measures. Suitable measures can include in particular the creation of covalent or ionic bonds between the polymer building blocks of the network; physical measures are also known, such as entanglement of the polymer building blocks.

The shaped hydrogel articles described in the prior art include, for example, eye implants which are either applied from the outside onto the surface of the eye (e.g. contact lenses) or are implanted into a layer or chamber of the eye (e.g. intraocular lenses). Examples of these are the shaped articles described in the patent documents cited below.

The ophthalmic implant from U.S. Pat. No. 5,127,901, for controlling gray cataract, is introduced between the sclera and the conjunctiva and has a suitable shape for this purpose.

The implants from U.S. Pat. No. 5,300,114 or U.S. Pat. No. 5,476,511 open up the possibility of allowing medically active substances to act beneath the conjunctiva. Ethylene/vinyl acetate copolymers are considered a particularly suitable polymer for the implant, which also presents a suitable diffusion barrier for the active substance to be released, which is located for example in an inner matrix made from this polymer. The membrane enclosing the matrix with the active substance is also constructed from this polymer. In addition, these implants contain an additive that indicates the consumption of the active substance. Moreover, these implants can also have coatings or sections at certain areas of the shaped article that are not permeable, not even temporarily, to the active substance, if this is so desired at certain areas of the eye.

The implants from U.S. Pat. Nos. 6,416,777 and 6,986,900 are introduced into the eye such that the medically active substance is arranged above the macula (yellow spot on the retina) and the implant is located outside the sclera. Their geometries have an F-shape, C-shape or L-shape. The interior containing the active substance can have a tablet shape, for example, and the polymer can be more or less permeable to the active substance, depending on the intended application. The polymer should be biocompatible and should not be biodegradable. Acrylates and silicones are mentioned as being preferred. In one variant, the active substance is dissolved in a fluid, such that provision has to be made for targeted delivery from the implant.

However, the requirements placed on shaped articles containing a medically active substance are not directly transferable to shaped articles into which analytes are intended to penetrate and be examined therein. In the latter case, in which analytes are intended to be detected by the shaped hydrogel article, the requirements are often the diametrical opposite of those for active substance implants, since the sensor material or materials are intended not to diffuse in the implant, or to diffuse only slightly, and instead they are intended to remain fixed in position in the implant. On the other hand, the analyte to be detected should be able to diffuse virtually unimpeded and rapidly to the site of detection in the implant, to ensure that the analyte concentration can be detected in real time. This is an essential requirement for allowing medical countermeasures to be taken, for example appropriate medication with insulin.

OBJECT OF THE INVENTION

The object of the present invention is therefore to make available a shaped hydrogel article that permits the detection of one or more analytes in a body fluid, for example an eye fluid, and at least substantially avoids the disadvantages of known shaped hydrogel articles. In particular, a shaped hydrogel article is to be made available whose external form and the rest of its structure make it possible for the hydrogel to accommodate, in addition to an analyte to be determined (e.g. glucose), also at least one sensor component and, if appropriate, at least one reference component.

DESCRIPTION OF THE INVENTION

This object is achieved by the invention having the features of the independent claim. Advantageous developments of the invention are characterized in the dependent claims. The wording of all the claims is hereby incorporated by reference into the content of this description.

A basic concept of the present invention lies in the immobilization of a sensor component in the implant by encapsulating the components in microparticles or nanoparticles that are distributed, in particular dispersed, in a hydrogel matrix. An at least substantially homogeneous distribution is particularly preferred.

An implant for detecting at least one analyte in a body fluid, in particular an eye fluid, is therefore proposed, the implant being designed to be implanted in a body tissue of a patient, in particular a tissue layer and/or a chamber of an eye of the patient. The term patient in this case includes in general living creatures, in particular humans, but does not necessary imply an illness. Thus, for example, measurements can also be carried out on healthy humans or animals, to measure a metabolite concentration in order, where appropriate, to be able to recognize illnesses in good time. However, the term implant is also intended to include the case where no implantation in the proper sense is actually performed, i.e. insertion into a tissue of a patient, and instead also includes simple application onto such a tissue, that is to say an application without the need for a surgical intervention, for example a contact lens and/or an inlay, which can be placed under a patient's eyelid, for example.

The implant has a hydrogel matrix with at least one hydrogel, the implant also having sensor particles dispersed in the hydrogel matrix, the sensor particles having at least one sensor matrix with a sensor matrix material (122) and at least one sensor material.

The sensor particles are preferably designed as microparticles or nanoparticles, preferably with a particle diameter in the range of a few micrometers (e.g. <100 micrometers, preferably <20 micrometers) to some 100 nanometers.

The microparticles or nanoparticles are preferably permeable to the analyte either on account of their structure or on account of a semipermeable shell. The interior of the particle is designed such that the sensor components have an optimal activity.

The sensor material is designed in such a way that it reacts sensitively to the analyte that is to be detected. This sensor property is preferably specific to the analyte that is to be detected. As is known from the prior art described above, different detection principles can be employed. For example, the analyte can react chemically with the sensor material (e.g. form a covalent bond, a complex bond or a similar connection), this bond being able to be detected, for example, by a change in the fluorescence properties of the analyte and/or of the sensor material and/or of the sensor material/analyte combination. Loose bonds are also possible, for example physical bonds and/or convergences of sensor material and analyte, which can in turn be detected by spectroscopy, for example. In each case, however, the sensor material is designed in such a way that at least one detectable physical and/or chemical property of the implant changes when the analyte concentration in the body fluid, in particular the eye fluid, changes or when analyte is present in the body fluid.

An important aspect and advantage of the invention is the fact that the properties of hydrogel matrix and sensor particles can be optimized separately. Thus, implants with good mechanical strength are needed, which, in the case of hydrogels, can be obtained principally by a higher network density and relatively low water content.

However, if relatively large biomolecules are used now for the sensor material, for example Con A (104 kD), glucose oxidase (63 kD), glucose dehydrogenase, hexokinase or glucose/galactose-binding protein (GGBP), whose functionality is dependent on the presence of the native configuration and on the mobility of the biomolecules, low water contents and dense networks have an unfavorable effect on the activity and mobility of the proteins. In the microparticles, the environmental conditions for such proteins and/or other sensor components can be optimized independently of the requirements of the implant. Moreover, the sensor material can also comprise a protein and/or a functionally equivalent fragment, mutants of hexokinase and/or GGBP and/or borate ester derivatives.

Thus, for example, hydrogels whose water content is over 90% can also be used for the microparticles or sensor particles. Since the proteins in such cases could partially diffuse out of the particles because of the low network density, the sensor particles are preferably coated with a semipermeable coating.

These can be "classical" LBL (layer-by-layer) coatings, but it is also possible to use crosslinked proteins, polysaccharides or other polymers that form a second, denser hydrogel layer around the interior of the particle. The term LBL also relates here to the consecutive deposition of oppositely charged polyelectrolytes. For example, a sensor particle can be coated first with a negatively or positively charged polyelectrolyte and then with an oppositely charged polyelectrolyte. This procedure can be repeated until the desired coating thickness and permeability is achieved, There are also variants in which partially uncharged polymer layers are incorporated between two oppositely charged coatings. Alternatively, the LBL coating can also be constructed not step by step, but instead in one step, by complexes of the two oppositely charged polyelectrolytes being formed in the coating solution and, under certain conditions, depositing on the surface of the particles. If the sensor components are very large, or if the hydrogel matrix enclosing the microparticies is particularly dense, then it is also possible to use mieroparticles without a membrane.

Suitable solutions for special sensor particles of this kind, in particular in the construction of the LBL coating, are disclosed in the following patent documents, for example: WO 2005/089727, WO 2004/014540, WO 02/0.17888, WO 00/077281, WO 00/003797, EP-A-1 116 516, WO 99/047252, WO 99/047253, U.S. Pat. Nos. 6,451,871, 6,896, 926, 7,022,379 and 6,926,965.

Suitable materials for sensor particles are, for example, ionically crosslinked alginates and mixtures of alginates and polysaccharides or polysaccharide derivatives such as carboxymethylcellulose, or also synthetic polymers or copolymers such as polyhydroxy ethyl methacrylate (P-HEMA), polyacrylamides and copolymers of acrylic acid and/or acrylic acid and methacrylic acid derivatives such as dimethylacrylamide, hydroxyethyl acrylate, methacrylic acid. All polymers that are water-soluble and cross-linked or crosslinkable can conceivably be used. It is also possible to use the same polymer for the sensor particles as for the hydrogel matrix, although the polymers should generally differ in terms of their degree of crosslinking. One example is polyvinyl alcohols with different quantities of functional, crosslinkable groups.

Suitable hydrogels for the sensor particles and/or also for the hydrogel matrix are disclosed in the following patent documents, for example: EP-B-0 641 806, EP-B-0 790 258, EP-B-0 807 265 and EP 0 637 490.

In addition to sensor particles with microparticles or nanoparticles that contain the sensor materials or sensor components, the implant preferably also has at least one reference component that is at least substantially analyte-invariant. The reference component can in particular have at least one luminescent component, in particular a fluorescence component. The luminescence properties of the luminescent component should be at least substantially analyte-invariant.

The reference component can in principle be introduced in different ways into the implant. For example, the reference component can be introduced in any desired manner into the hydrogel matrix or sensor matrix, for example dispersed, dissolved, emulsified or suspended in the matrix. A chemical bond, for example a covalent bond, an ionic bond or a complex bond, to one or more components of the implant, for example to the hydrogel matrix, is also possible.

In a particularly preferred embodiment, the at least one reference component is introduced into the implant by means of reference particles. Reference particles can thus be embedded in the hydrogel matrix, which reference particles contain one or more reference components. Moreover, a reference matrix material can be contained. These reference particles can in turn preferably have microparticles or nanoparticles, preferably with a particle diameter in the range of a few micrometers (e.g. <100 micrometers, preferably <10 micrometers) to some 100 nanometers.

In principle, the comments that have been made above in respect of the hydrogel matrix can apply accordingly for the reference matrix material. In particular, one or more of the materials described above can also be used for the reference matrix material. The use of a shell around the reference particle is also once again possible, and, as regards the materials and other properties, reference can once again be made to the comments made above regarding the shell of the sensor particles. The sensor and/or reference particles should be relatively small in relation to the thickness of the shaped hydrogel article, so as to permit a homogeneous distribution in the hydrogel and reference matrix material. The diameter should preferably not be greater than ca. 10% of the thickness of the hydrogel or of the shaped hydrogel article.

The reference components can be or can comprise fluorescence dyes or high-molecular-weight derivatives of fluorescence dyes, for example, which are chemically or physically bound on the surface of the hydrogel, of the sensor particles and/or of the reference particles or in the matrix (matrix material) of the reference or sensor particles.

Preferably, the reference components are at least substantially analyte-invariant, i.e. their detectable physical and/or chemical properties (e.g. once again fluorescence and/or luminescence properties) do not essentially change, or change only inappreciably (e.g. by not more than 5%, preferably less) even in the presence of the analyte that is to be detected.

For the surface bonding of the dyes, covalent bonds can be used, but also strong complex bonds such as biotin-avidin. In these cases, functional groups on the surface of the particles are reacted with functional groups on the dye molecule. Corresponding synthesis procedures for coupling of, for example, amino groups, thiol groups and carboxyl groups are known in the literature. The dyes can also be embedded in LBL coatings or other coatings that are applied to inert particles. In these cases, the dye can either be deposited together with the polyelectrolytes on account of its charging properties, for example, or the dye is covalently bonded directly onto one of the polyelectrolytes.

For the bonding in the particles, the reference components (hereinafter also simply called "dyes" or "dye molecule" or "dye group" without restricting the general nature of the possible embodiments) can be polymerized directly with monomers, for example, and embodied as particles. In this case, the network arising from the polymerization of the monomers is preferably so narrow-meshed that the dye molecule can no longer diffuse out. Such physical immobilization can also be achieved by swelling of the particles in suitable solvents and by incubation of the swollen particles in a dye solution. Use is made of the fact that the network increases its pore size in suitable solvents (e.g. polystyrene in toluene) and, after inward diffusion of the dye molecules in the solvent (water or physiological solution), again reduces the pore size. This is of advantage particularly in the case of sensitive dyes, since the conditions of polymerization are circumvented.

Another variant is one in which the dye molecule itself contains polymerizable functional groups and is copolymerized together with the monomer. The reference particles are distinguished by the fact that their measurement parameter, e.g. fluorescence, does not change with the concentration of the analyte.

The implant can in particular have a shaped hydrogel article. The shaped hydrogel article itself is then preferably produced from a water-soluble crosslinkable prepolymer and the sensor and reference particles. The particles are dispersed homogeneously in an aqueous solution of the prepolymer, and the aqueous dispersion is then crosslinked (free-radical crosslinking, e.g. photochemically or thermally or in 2+2 cycloaddition).

The shaped article preferably has a maximum diameter of 10 mm and a surface-to-volume ratio of at least 8. This development of the invention has the effect that the speed of response of the implant to changes of the analyte concentration of the eye fluid does not typically exceed a value of a few minutes, preferably of not more than 3-4 minutes. The shaped article does not necessarily have to be a round disk. Instead, any desired shapes are possible, as long as the circle circumscribing the shape is not greater than 10 mm.

The edge of the shaped article can be substantially right-angled, although "substantially" also allows for deviations of up to 60°, but preferably of not more than 20°, and particularly of not more than 5°. The thickness of the shaped article preferably decreases toward the edge. The edge has a preferred angle of 0° to 60°. The rims can preferably be rounded. The shaped article can be planar or curved. The curve preferably has a radius of curvature of 14 mm to 8 mm. The radius of curvature of the curve should in particular be not less than 8 mm.

Illustrative Embodiments

Further details and features of the invention will become evident from the following description of preferred illustrative embodiments in conjunction with the dependent claims. Here, the respective features can be embodied singly or in combination with one another. The invention is not restricted to the illustrative embodiments.

The illustrative embodiments are depicted schematically in the figures. The same reference numbers in the individual figures designate identical elements or elements that have an identical function or that correspond in terms of their function.

Figure 1:
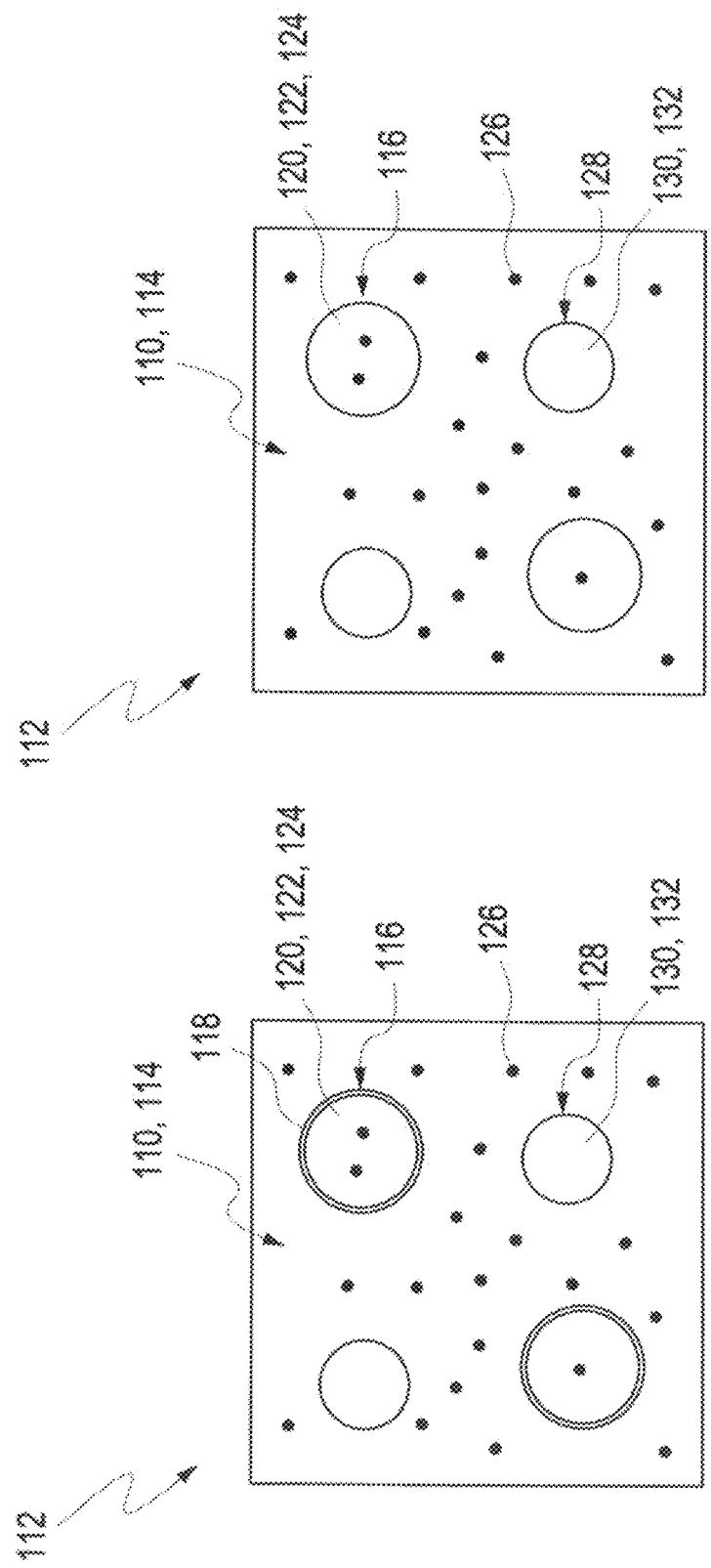
FIG. 1A shows a hydrogel matrix of an implant with sensor particles with a membrane.
FIG. 1B shows a hydrogel matrix of an implant with sensor particles without a membrane.

FIGS. 1A and 1B each show a hydrogel matrix 110 of an implant 112 (the implant is only represented symbolically). Hereinbelow, the application of the invention to an eye implant is specifically explained; however, as indicated above, the invention can in principle also be used on implants 112 for other types of body tissue. The hydrogel matrix 110 of the implant 112 in each case has a hydrogel 114 as its main component. The water content, the network density and the shape of the hydrogel matrix 10 can each be optimized for the particular implantation application.

In both cases, sensor particles 116 are distributed in the hydrogel matrix 110. The illustrative embodiments in FIGS. 1A and 1B differ from each other in that the sensor particles 116 in FIG. 1A have a membrane 118, while those in the illustrative embodiment in FIG. 1B do not. Embodiments are also conceivable, however, in which sensor particles 116 with a membrane 118 and also others without a membrane are present alongside one another.

The sensor particles 116 each have a sensor matrix 120 with a sensor matrix material 122 and a sensor material 124 received in the sensor matrix material. The sensor material 124 is sensitive to an analyte 126, which is indicated symbolically in FIGS. 1A and 1B by reference number 126 and which can diffuse through the hydrogel matrix 110 and preferably also through the sensor matrix 120.

The at least one sensor matrix material (122) and the hydrogel matrix (110) are designed in such a way that the at least one sensor material (124) has a higher diffusion coefficient in the sensor matrix material (122) that in the hydrogel matrix (110), in particular than in the at least one hydrogel (114) of the hydrogel matrix (110).

In the illustrative embodiments shown, reference particles 128 are also distributed in the hydrogel matrix 110. They have a reference matrix material 130 and a reference component 132, the reference component 132 in this illustrative embodiment being physically and/or chemically bonded on the surface and/or in the interior of the reference matrix material 130. For example, a fluorescence dye can be polymerized in as reference component 132, and/or a fluorescence dye applied to the surface of the reference matrix material 130 and/or of the reference particle 128 can be used as reference component 132.

Figure 2:
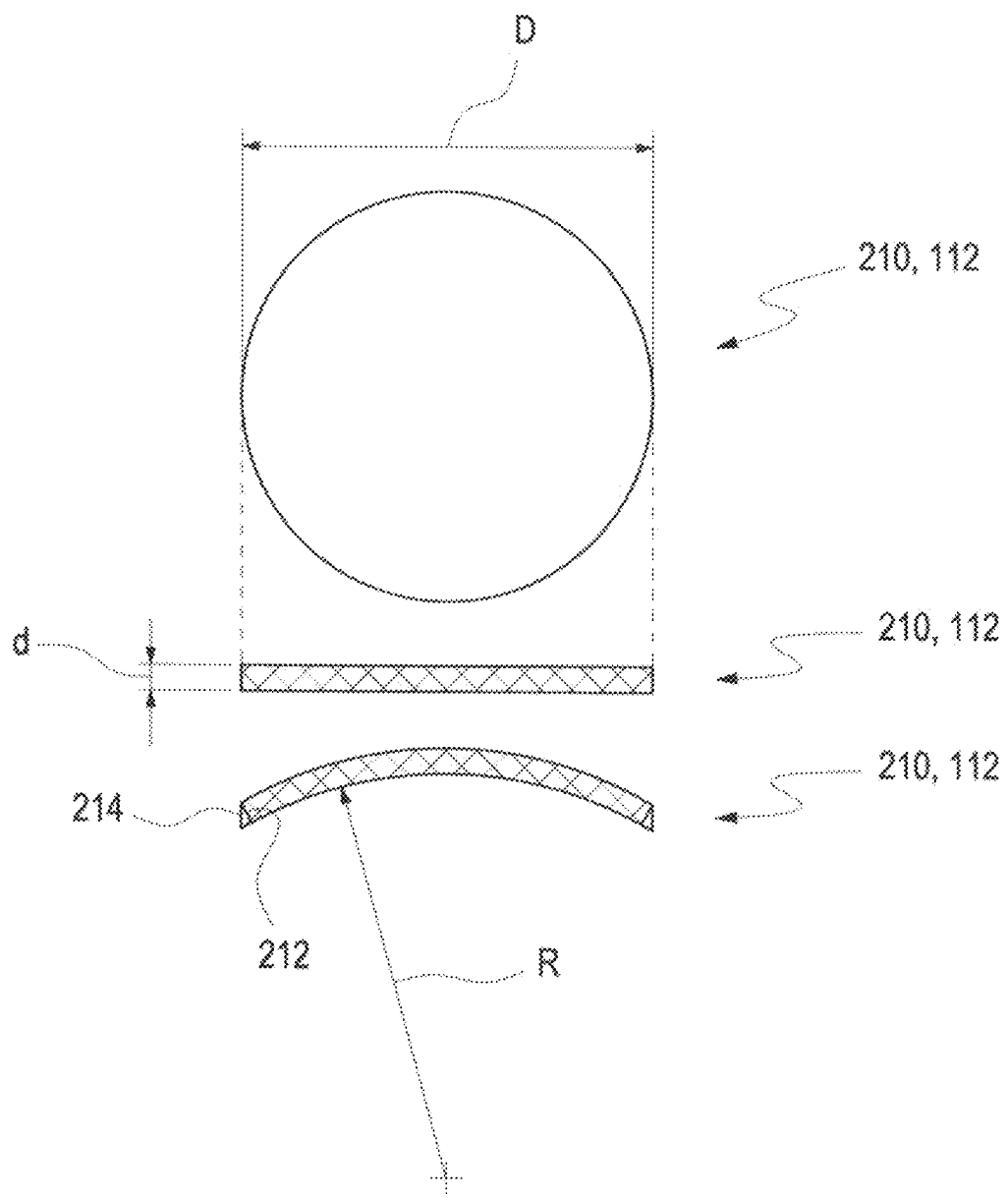
FIG. 2 shows a shaped article of an implant in different views.

In FIG. 2, an illustrative embodiment of a shaped article 210 of an implant 112 is shown in different views. The view at the top is a plan view, the view in the middle is a cross-sectional view from the side without curvature, and the view at the bottom is a cross-sectional view from the side with a curvature. The diameter D is preferably not more than 10 mm, and the thickness d is preferably ca. 250 micrometers. The radius of curvature R (view at the very bottom) is preferably between 8 mm and 14 mm.

In the view of the shaped article 210 at the very bottom, two possible edge shapes are also shown superposed. While the edge shape 212 is a substantially right-angled edge, as can be generated for example by means of a casting mold, the edge shape 214 is a tapered shape. Here, the margins of the edge shape 214 are preferably perpendicular to a disk plane of the shaped article 210. Such an edge profile 214 can be created, for example, by a lithographic production technique in which the shaped article 210 is cured by being irradiated perpendicularly from above.

Figure 3:
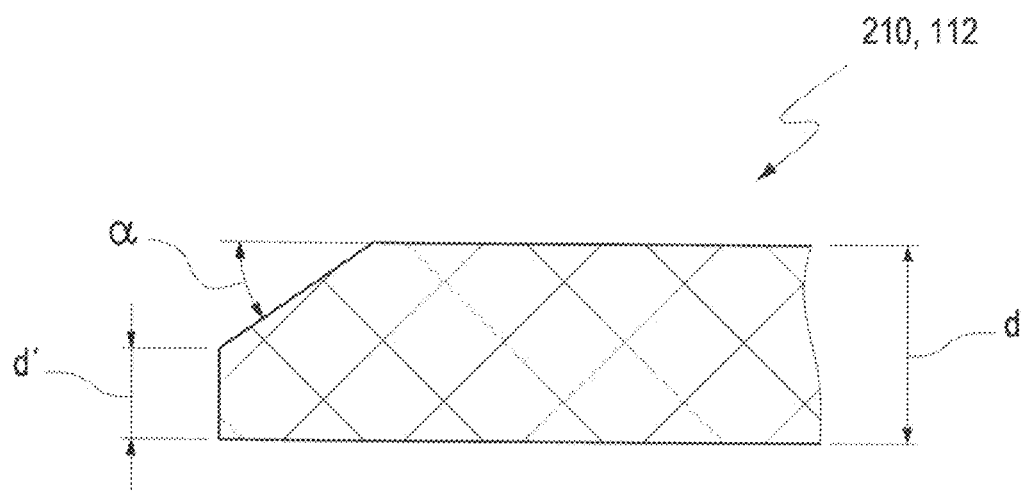
FIG. 3 shows a cross-sectional view of a first illustrative embodiment of a shaped article of an implant in a side view.
Figure 4:
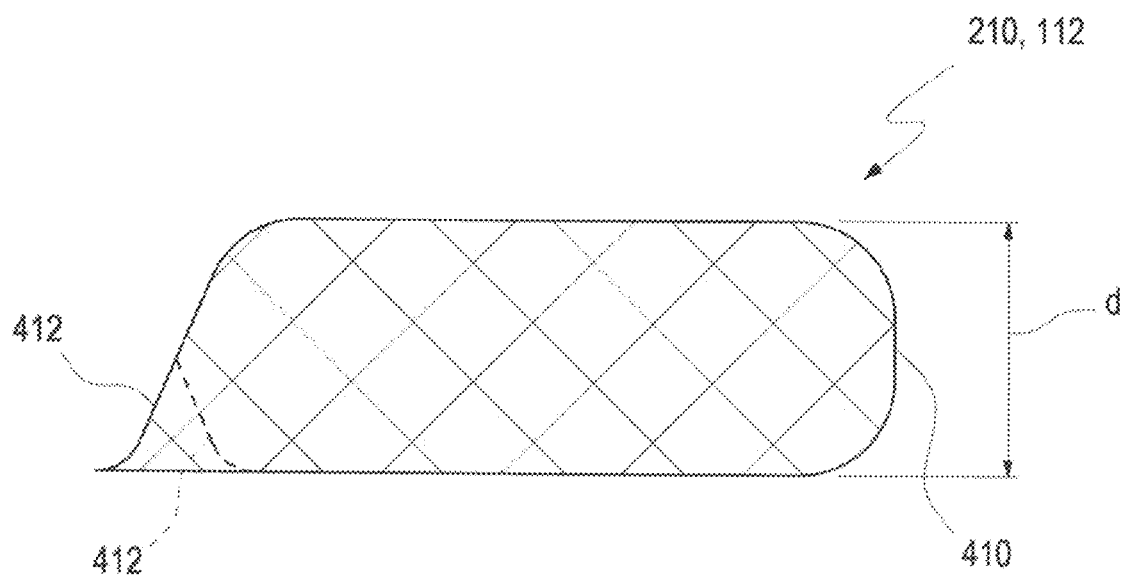
FIG. 4 shows a cross-sectional view of a second illustrative embodiment of a shaped article of an implant in a side view.

FIGS. 3 and 4 show other illustrative embodiments of edge configurations of a shaped article 210. Thus, FIG. 3 shows a partially oblique edge shape. The thickness of the shaped article 210 decreases from the starting thickness d to the thickness d' toward the edge. While the thickness d can be 250 micrometers, for example, the edge thickness d' can, for example, be from 15 micrometers to 250 micrometers. This results, for example, in an edge angle, designated by α in FIG. 3, of from 0° to 60°.

FIG. 4 in turn shows two possible edge profiles 410, 412 of a shaped article 210, which can be used in other illustrative embodiments. Here, reference number 410 designates an edge geometry which (for example by using a suitable casting mold) has a rounded (e.g. circular arc-shaped or elliptic) profile. Reference number 412 designates an edge geometry that has a curved profile, for example by using a laser ablation technique. This curved profile 412 can be provided at one side (solid line 412) or also at both sides (shown by broken line in FIG. 4).

The form of the shaped hydrogel article 210 can be defined, for example, by a suitable casting mold. The casting mold is preferably produced such that a shrinkage or swelling during curing of the starting formulation is taken into account. The casting mold can be made entirely or partially of a plastic such as polypropylene (PP), polymethylmethacrylate (PMMA), polycarbonate (PC), polyoxymethylene (POM) or polyether-esterketone (PEEK) or of glass (transmitting UV light). In the case of closed molds, the edge geometry is defined by the closed casting mold. In the case of open molds (glass molds), the edge can be defined by UV crosslinking in photolithography or by the surface tension between prepolymer solution and mold material.

In the case of open molds or larger mold sections, the edge can also be defined by being cut out. A mechanical cutting results in a substantially right-angled edge geometry. When cutting by means of laser, a "rounded" edge can be obtained using a Gaussian intensity profile.

Examples of the production of a shaped hydrogel article are explained below.

EXAMPLE 1

Production of Alginate Hydrogel Particles for the Sensor Components

Alginic acid sodium salt is dissolved with stirring in deionized water at 55° C. The alginate solution is sprayed by means of a two-fluid atomizer (Spraying Systems Co.) into an ultrasound bath filled with calcium chloride solution, where the alginate droplets set.

The set alginate particles are filtered through a 30 μm filter cloth, and the filtrate is concentrated by settling in the separating funnel. The alginate particles are then autoclaved as a 10% strength solution. Depending on the desired water content of the alginate particles, the concentration of the alginate solution can be varied between 0.2% and 10%. By suitable choice of the alginate type (molecular weight, ratio of guluronic acid to mannuronic acid), further fine-tuning of the network density is possible.

EXAMPLE 2

Optional Precoating of the Alginate Particles

The alginate particles are centrifuged off and are mixed in the ratio 1:1 (w/v) with polyallylamine hydrochloride in 10 mM acetate buffer, pH 5.5, and incubated for 5 minutes. The mixture is centrifuged, the supernatant is removed, and the alginate particles are washed twice, in each case for 2 minutes, in the ratio 1:2 (w/v) with 10 mM acetate buffer, pH 5.5, and centrifuged off. This procedure is repeated with polystyrene sulfonate in 10 mM acetate buffer, pH 5.5, as second coat. The procedure is repeated until the desired number of coats have been applied. The number of coats and the concentration of the polyelectrolytes determine the density of the precoating. Typical concentrations are between 0.05% and 1%, typical coat numbers between 1 and 6.

EXAMPLE 3

Filling the Precoated Alginate Spheres with Sensor Components Dextran and ConA

The (optionally precoated) alginate particles are centrifuged off, washed once with deionized water and are again centrifuged off.

The required amount of dextran is weighed out and dissolved in water.

1 ml of the dextran solution is added to 1 g of the centrifuged pellet of alginate particles, mixed by agitation, homogenized in an ultrasound bath, and incubated overnight at 2-8° C. The alginate spheres are then centrifuged off and separated from the supernatant. The amount of dextran taken up is calculated from the difference between the specific absorptions of supernatant before and after charging. Typical charges are between 0.01 and 10 mg of dextran per g of alginate particles.

ConA is dissolved in a concentration of 5-15 mg/ml in TRIS buffer, pH 7.4. The required amount of ConA is added to the dextran-filled pellet of alginate particles, mixed by agitation, homogenized in an ultrasound bath, and incubated overnight at 2-8° C. The alginate spheres are then centrifuged off and separated from the supernatant. The amount of ConA taken up is calculated from the difference between the protein-specific absorptions of supernatant before and after charging.

EXAMPLE 4

Coating of the Alginate Particles

The charged (optionally precoated) alginate spheres are mixed in the ratio 1:1 (w/v) with polystyrene sulfonate in 10 mM acetate buffer, pH 5.5, and incubated for 5 minutes. The mixture is centrifuged, the supernatant is removed, and the alginate spheres are washed twice, in each case for 2 minutes, in the ratio 1:2 (w/v) with 10 mM acetate buffer, pH 5.5, and centrifuged off. This procedure is repeated alternately with polyallylamine hydrochloride in 10 mM acetate buffer, pH 5.5, and polystyrene sulfonate in 10 mM acetate buffer, pH 5.5, until the desired number of coats have been applied. The number of coats and the concentration of the polyelectrolytes determine the density of the precoating. Typical concentrations are between 0.05% and 1%, typical coat numbers between 10 and 60.

EXAMPLE 5

Preparation of the Formulation

A 10% strength suspension of reference particles is homogenized in an ultrasound bath.

990 mg of coated sensor particles are mixed, by stirring, with 8.4.15 g of a 20 to 40% strength solution of acrylamidoacetaldehydo-1,3-acetal of polyvinyl alcohol. 495 μl of a 10% strength suspension of reference particles are pipetted in, and the mixture is homogenized in an ultrasound bath. The formulation is then rolled for ca. 3 hours on a roller block.

EXAMPLE 6

Production of Implants

The formulation is introduced into a syringe and, by means of a metering unit driven by compressed air, is metered into a shaped article (female side BK7 glass, male side quartz glass). The shaped article is closed and irradiated for ca. 5 second under UV light (Hamamatzu mercury-xenon lamp). The crosslinked implant is removed from the shaped article, air-dried and packaged.

Implants with diameters of 2 mm and 4 mm and a thickness of ca. 140 to 250 μm have already been produced and implanted in the human eye. Implants with radii of curvature of 12 mm and 8.6 mm and planar implants have been used. The edges are defined by punching or by form fit.

Edges with bevels on the top and bottom are also used. Cutting by means of excimer laser is also carried out.

LIST OF REFERENCE NUMBERS 110 hydrogel matrix
112 implant.

114 hydrogel
116 sensor particle
118 membrane
120 sensor matrix
122 sensor matrix material
124 sensor material
126 analyte
128 reference particle
130 reference matrix material
132 reference component
210 shaped article
212 right-angled edge shape
214 tapered edge shape
410 round edge profile
412 curved edge profile

The invention claimed is:

1. An implant for detecting at least one analyte in a body fluid, the implant being designed to be implanted in a body tissue of a patient, the implant comprising a hydrogel matrix with at least one hydrogel and sensor particles dispersed homogeneously in the hydrogel matrix, wherein the sensor particles comprise at least one sensor matrix comprising a sensor matrix material and at least one sensor material, the implant further comprising reference components also dispersed homogeneously in the hydrogel matrix, wherein the reference components are at least substantially analyte-invariant.

2. The implant as claimed in claim 1, the sensor material comprising at least one of the following materials: concanavalin A; glucose oxidase; glucose dehydrogenase; hexokinase; glucose/galactose-binding protein; a protein and/or a fragment functionally equivalent to a protein; a mutant of hexokinase; a mutant of glucose/galactose-binding protein; and a borate ester derivative.

3. The implant as claimed in claim 1, the sensor particles comprising a shell that is at least partially permeable to the analyte.

4. The implant as claimed in claim 1, the sensor material comprising at least one of the following materials:
 a molecule and/or a group which, in the presence of an analyte, changes at least one chemical or physical property;
 a molecule and/or a group where the analyte, on approaching and/or reacting with the molecule and/or the group, changes at least one chemical or physical property; and
 a molecule and/or a group where the analyte undergoes a chemical or physical bonding to the molecule and/or the group, which bonding can be detected by a change in at least one chemical or physical property.

5. The implant as claimed in claim 1, the sensor matrix material. comprising at least one of the following materials; an alginate; a polysaccharide; a polysaccharide derivative; a synthetic polymer; a copolymer crosslinked covalently or via a hydrogen bond; an ionically crosslinked polymer or copolymer; a polyacrylamide; a copolymer containing an acrylic acid unit; an acrylic acid derivative; and a methacrylic acid derivative.

6. The implant as claimed in claim 1, wherein the reference component comprises at least one luminescent component, wherein the luminescence properties of the luminescent component are at least substantially analyte-invariant.

7. The implant as claimed in claim 1, wherein the implant comprises reference particles implanted in the hydrogel matrix, the reference particles comprising the at least one reference component, the reference component comprising, at least one reference matrix material, and wherein the reference component is bonded physically and/or chemically on the surface and/or the interior of the reference matrix material.

8. A method for detecting at least one analyte in a body fluid, comprising implanting an implant according to claim 1 in a body tissue and detecting the at least one analyte using qualitative or quantitative detection.

9. The implant as claimed in claim 1, wherein the implant is for detecting an eye fluid and the implant is designed to be implanted to a chamber of an eye the patient.

10. The implant as claimed in claim 3, the shell being substantially impermeable to the at least one sensor material.

11. The implant as claimed in claim 3, the shell comprising at least one of the following materials: a crosslinked protein; a polysaccharide; a crosslinked polysaccharide; a hydrogel with a density exceeding the density of the hydrogel of the hydrogel matrix; and a layer-by-layer coating.

12. The implant as claimed in claim 4, wherein the at least one chemical or physical property is a fluorescence property.

13. The implant as claimed in claim 7, wherein the physical and/or chemical bond comprises at least one of the following bonds: a covalent bond; a complex bond; an ionic interaction and/or an ionic bond.

14. The implant as claimed in claim 7, wherein the reference component is connected to the reference matrix material at least partially by polymerization.

15. The implant as claimed in claim 7, wherein the reference component is at least substantially immobilized physically in the reference matrix material.

16. An implant for detecting at least one analyte in a body fluid, the implant being designed to be implanted in a body tissue of a patient, the implant comprising a hydrogel matrix with at least one hydrogel and sensor particles dispersed in the hydrogel matrix, wherein the sensor particles comprise at least one sensor matrix comprising a sensor matrix material and at least one sensor material, wherein the at least one sensor material has a higher diffusion coefficient in the sensor matrix material than in the hydrogel matrix.

17. The implant as claimed in claim 16, wherein the sensor matrix material has a lower density than the hydrogel matrix.

18. An implant for detecting at least one analyte in a body fluid, the implant being designed to be implanted in a body tissue of a patient, the implant comprising a hydrogel matrix with at least one hydrogel and sensor particles dispersed in the hydrogel matrix, wherein the sensor particles comprise at least one sensor matrix comprising a sensor matrix material and at least one sensor material, wherein the sensor matrix material comprises a hydrogel with a water content that exceeds the water content of the hydrogel of the hydrogel matrix.

19. The implant as claimed in claim 18, wherein the hydrogel of the sensor matrix material has a water content of at least 70 percent by weight.

20. An implant for detecting at least one analyte in a body fluid, the implant being designed to be implanted in a body tissue of a patient, the implant comprising hydrogel matrix with at least one hydrogel and sensor particles dispersed in the hydrogel matrix, wherein the sensor particles comprise at least one sensor matrix comprising a sensor matrix material and at least one sensor material, wherein the hydrogel matrix and the sensor matrix material comprise a chemically identical hydrogel, wherein the hydrogel of the hydrogel matrix has a higher degree of crosslinking than the hydrogel of the sensor matrix material.

21. An implant for detecting at least one analyte in a body fluid, the implant being designed to be implanted in a body tissue of a patient, the implant comprising as hydrogel matrix with at least one hydrogel and sensor particles dispersed homogeneously in the hydrogel matrix, wherein the sensor particles comprise at least one sensor matrix comprising a sensor matrix material and at least one sensor material, wherein the implant has a shaped hydrogel article, the shaped hydrogel article having a substantially flat, round configuration, the diameter of the shaped hydrogel article being not greater than 10 mm, and wherein the shaped hydrogel article has a surface-volume ratio of at least 5.

22. An implant for detecting at least one analyte in a body fluid, the implant being designed to be implanted in a body tissue of a patient, the implant comprising a hydrogel matrix with at least one hydrogel and sensor particles dispersed homogeneously in the hydrogel matrix, wherein the sensor particles comprise at least one sensor matrix comprising a sensor matrix material and at least one sensor material, wherein the implant has a shaped hydrogel article, the shaped article having a substantially right-angled edge.

23. An implant for detecting at least one analyte in a body fluid, the implant being designed to be implanted in a body tissue of a patient, the implant comprising a hydrogel matrix with at least one hydrogel and sensor particles dispersed homogeneously in the hydrogel matrix, wherein the sensor particles comprise at least one sensor matrix comprising a sensor matrix material and at least one sensor material, wherein the implant has a shaped hydrogel article, the shaped hydrogel article having a substantially flat, round configuration, the diameter of the shaped hydrogel article being not greater than 10 mm, wherein the shaped article has a curve with a radius of curvature of between 5 mm and 20 mm.

24. An implant for detecting at least one analyte in a body fluid, the implant being designed to be implanted in a body tissue of a patient, the implant comprising a hydrogel matrix with at least one hydrogel. and sensor particles dispersed homogeneously in the hydrogel matrix, wherein the sensor particles comprise at least one sensor matrix comprising a sensor matrix material and at least one sensor material, wherein the implant has a shaped hydrogel article, the shaped hydrogel article having a substantially flat, round configuration, the diameter of the shaped hydrogel article being not greater than 10 mm, wherein the edge area of the shaped article has a thickness of not more than 250 micrometers.

25. An implant for detecting at least one analyte in a body fluid, the implant being designed to be implanted in a body tissue of a patient, the implant comprising a hydrogel matrix with at least one hydrogel and sensor particles dispersed homogeneously in the hydrogel matrix, wherein the sensor particles comprise at least one sensor matrix comprising a sensor matrix material and at least one sensor material, wherein the implant has a shaped hydrogel article, the shaped hydrogel article having a substantially flat, round configuration, the diameter of the shaped hydrogel article being not greater than 10 mm, wherein the shaped article has a rounded edge.

* * * * *